United States Patent
Defrance

(10) Patent No.: US 9,700,574 B2
(45) Date of Patent: Jul. 11, 2017

(54) USE OF SECNIDAZOLE IN TREATMENT OF DENTAL INFECTIONS

(75) Inventor: Pierre-Marie Defrance, Aix en Provence (FR)

(73) Assignee: ATHENA PHARMACEUTIQUES SAS, Louveciennes (FR)

( * ) Notice: Subject to any disclaimer, the term of this patent is extended or adjusted under 35 U.S.C. 154(b) by 0 days.

(21) Appl. No.: 14/115,923

(22) PCT Filed: May 14, 2012

(86) PCT No.: PCT/FR2012/000192
§ 371 (c)(1),
(2), (4) Date: Nov. 6, 2013

(87) PCT Pub. No.: WO2012/156599
PCT Pub. Date: Nov. 22, 2012

(65) Prior Publication Data
US 2014/0080778 A1    Mar. 20, 2014

(30) Foreign Application Priority Data
May 16, 2011  (FR) ..................... 11 01478

(51) Int. Cl.
*A61K 31/7052* (2006.01)
*A61K 31/4164* (2006.01)
*A61K 9/00* (2006.01)
*A61K 31/7048* (2006.01)
*A61K 45/06* (2006.01)

(52) U.S. Cl.
CPC ........ *A61K 31/7052* (2013.01); *A61K 9/0053* (2013.01); *A61K 31/4164* (2013.01); *A61K 31/7048* (2013.01); *A61K 45/06* (2013.01)

(58) Field of Classification Search
CPC ............ A61K 31/7052; A61K 31/4164; A61K 9/0053; A61K 31/7048
See application file for complete search history.

(56) References Cited

U.S. PATENT DOCUMENTS 7,691,831 B2 * 4/2010 Bonner, Jr. ............ A61K 31/52
514/152

FOREIGN PATENT DOCUMENTS

CN    1559428 A    1/2005

OTHER PUBLICATIONS

Hirsch, "Periodontal healing and bone regeneration in response to azithromycin", Australian Dental Journal, vol. 55, issue2, 2010, pp. 193-199.*
Gad et al., "Rormulation and Evaluation of Secnidazole or Doxycycline Dento-Oral Gels", Drug Development and Industrial Pharmacy, vol. 34, No. 12, 2008, pp. 1356-1367.*
Malhotra et al, "Ciprofloxacin-Tinidazole Combination, Fluconazole-Azithromycin-Secnidazole-Kit and Doxycycline-Metronidazole Combination Therapy in Syndromic Management of Pelvic Inflammation Disease: A prospective Randomized Controlled Trial", Indian Journal of Medical Sciences, vol. 57, No. 12, Dec. 2003, pp. 549-555.*
Poulet et al., "Concentrations and in vivo antibacterial activity of spiramycin and metronidazole in patients with periodontitis treated with high-dose metronidazole and the spiramycin/metronidazole combination", Journal of Antimicrobial Chemotherapy, vol. 55, No. 3, 2005, pp. 347-351.*
Sharma et al., Arch. Gynecol. Obstet., 2006, p. 273, p. 232-235.*
Silva et al., Rev. Hosp. Clin. Fac. Med. S. Paulo, 2002, 57(1), p. 9-14.*
Hopkins, S., Am J. Med., 1991, 91(3, S1), p. 40S-45S.*
Gillis et al., Drugs, 1996, 51(4), p. 621-638.*
Gad, H. et al.,"Formulation and Evaluation of PLA and PLGA in Situ Implants Containing Secnidazole and/or Doxycycline for Treatment of Perodontitis", AAPS PharmSciTech, vol. 9, No. 3, Sep. 2008, pp. 878-884.
International Search Report for International Application No. PCT/FR2012/000192, International Filing Date: May 14, 2012; Date mailed: Jun. 8, 2012; 3 pages.
Rotzetter, PA, et al.,"Kinetics of spiramycin/metronidazole (Rodogyl) in human gingival crevicular fluid, saliva and blood", J. Clin. Periodontal 1994; vol. 21; pp. 595-600.
Written Opinion of the International Searching Authority for International Application No. PCT/FR2012/000192, International Filing Date: May 14, 2012; Date mailed: Jun. 8, 2012; 9 pages.
Yin, L. et al., "Clinical investigation of secnidazole in treatment of oral anaerobic infection", Stomatology, vol. 28, No. 11, Nov. 2008, pp. 596-598.

* cited by examiner

*Primary Examiner* — Jonathan S Lau
(74) *Attorney, Agent, or Firm* — Cantor Colburn LLP

(57) ABSTRACT

The invention relates to the combination of secnidazole with an antibiotic of the macrolide family, preferably azithromycin 11, for oral treatment of dental infections, which enables a considerable reduction in the length of treatment and the doses administered in comparison with the conventional treatment.

4 Claims, No Drawings

USE OF SECNIDAZOLE IN TREATMENT OF DENTAL INFECTIONS

The present invention is about treatment of acute, chronic or recurring stomatologic infections such as:
- dental abscess, phlegmon, perimaxillary cellulitis, pericoronaris
- gingivitis, stomatitis
- parodontitis
- parotiditis, sub-maxillitis
- etc.

The most common treatment used now is associating a nitroimidazole (i.e. metronidazole), and an antibiotic of the macrolide group (i.e. spiramycine). J. Clin. Periodontol 1994; 21; 595-600 reports the result from studies on the metronidazole/spiramycine association, branded as RODOGYL® spiramycine, used in the treatment of parodontitis. According to this document, the RODOGYL® spiramycine used, especially prepared, contains 739,000 IU of spiramycine and 127.4 mg of metronidazole (page 596, central column, $2^{nd}$ paragraph).

Moreover, it appears in the same document that the oral treatment studied lasts 3 days and includes the administration of 6 tablets on the $1^{st}$ day, 6 tablets on the $2^{nd}$ day and 3 tablets on the $3^{rd}$ day (page 596, column on the right, second to last paragraph), i.e. a total of 15 tablets, which represent:
- 11 085 000 IU (=3454 mg) of spiramycine (4.10 times the molar mass of this macrolide antibiotic), and
- 1911 mg of metronidazole.

It would be advisable to alleviate the treatment, and this is the objective of the present invention.

Secnidazole, or alpha-2-dimethyl-5-nitro-1H-imidazole-1-ethanol, is indicated in the treatment against amoebiasis, trichomoniasis and giardiasis (Jane C. Gillis et al, Data Embase [online] EMB-1996113854 and M L M Gonzales et al, Data Embase [online] EMB-2009489088).

Although secnidazole is closed to metronidazole on a structural point of view, it has not been considered till date to use it in the oral treatment of stomatologic infections in association with an antibiotic of the macrolide family.

Yet it has appeared to the applicant that secnidazole could be used to alleviate the treatment of such infections, given its long half-life in the body, and the applicant also noted that not only a single dose of secnidazole presents a benefice-risk ratio at least equivalent to the present treatment of reference, but also in an unexpected way, that the concomitant administration of the antibiotic of the macrolide group can also be lowered to 1 day instead of 3-4 days.

By "single dose" is meant a one-day only treatment, with one intake or possibly two intakes.

The single dose will comprise generally 1500 mg to 2500 mg, and preferably 2000 mg of secnidazole.

Therefore the invention focuses on the use of secnidazole in association with an antibiotic of the macrolide group, in order to obtain a single unit drug or a pair of drugs intended to the oral treatment of stomatologic infections.

This antibiotic can be spiramycine as it is in the association, fallen in the public domain, exploited under the brand name RODOGYL® spiramycine, and in which nobody before the applicant had the idea to substitute secnidazole to metronidazole, whereas it is known for a long time that secnidazole plasma half-life is higher than metronidazole half-life. The only structure similarity was therefore not a sufficient incentive for one skilled in the art.

The absence of evidence for this substitution is even greater than we had yet already considered the use of secnidazole in the treatment of dental infection.

Thus, Drug Development and Industrial Pharmacy, 34: 1356-1367, 2008—pages 1356 to 1367) provides an evaluation of secnidazole formulated in a oro-dental gel for an administration directly in the periodontal pocket.

However, the planned use according to this document is:
- not oral (=systemic) as proposed in the present invention, but local, and in addition, using a method that can be implemented by a Health Professional only, not by the patient himself, since the gel is to be syringue-injected in the periodontal pocket,
- not associating secnidazole to a antibiotic of the macrolide type, but using it alone,
- without precising the treatment duration or the number of injections, all the reported tests being in vitro tests [the only intervention on patients (column on the left p. 1359) being a sampling for in vitro culture and test], and
- without precising the quantity of secnidazole required for the treatment: the document only indicating that the minimal inhibition concentration for the tested microorganisms is 0.125-5 µg of secnidazole per ml of gel.

This article from Drug Development and Industrial Pharmacy that describes only a gel for local application and containing only secnidazole cannot suggest by implicit reference to vaginosis treatment (reference cited Gillis & Wiseman1), to substitute secnidazole to metronidazole in the association reported in J. Clin. Periodontol 1994: 21: 595-600 in order to change the treatment duration from 3 days to 1 day, and to reduce considerably the quantity of antibiotic.

[1] Gillis, J. C. & Wiseman L. R. (1996) Secnidazole: A review of its antimicrobial activity, pharmacokinetic properties and therapeutic use in the management of protozoal infections and bacterial vaginosis. Drugs, 51, 621-638.

AAPS PharmaSciTech, Vol. 9, No. 3, September 2008—pages 878 to 884, which authors are the same as for the article from Drug Development and Industrial Pharmacy analysed above, repeats verbatim a part of this latter, the difference between the two being however that, instead of administering the gel with a syringe in the periodontal pocket, the authors recommend the insertion of an implant created in situ in said pocket, implant that associates secnidazole and doxycycline hydrochloride.

Doxycycline is not a macrolide but a tetracycline. The antibiotic associated to secnidazole does not belong to the same category as the ones planned in the invention. Regarding reference 12 cited in AAPS PharmaSciTech, relative to secnidazole half-life, it is exactly the reference Gillis & Wiseman cited in the article from Drug Development and Industrial Pharmacy: it concerns vaginosis treatment.

In summary, except the idea to associate an antibiotic to secnidazole, the article from AAPS PharmaSciTech does not bring more information than the article from Drug Development and Industrial Pharmacy, since the use planned according to the article from AAPS PharmaSciTech is:
- not oral (=systemic) as proposed in the present invention, but local, and in addition, using a method that can be implemented by a Health Professional only, not by the patient himself, since it implies the creation in situ of the implant in the periodontal pocket,
- not associating secnidazole to an antibiotic of the macrolide type, but with an antibiotic of the tetracycline type,
- without precising the treatment duration or the number of implantations, all the reported tests being in vitro tests

[the only intervention on patients (column on the left p. 880) being a sampling for in vitro culture and test] (the article from AAPS PharmaSciTech does not claim anyway that in vivo results were obtained: it only indicates on page 883, right column, end of $3^{rd}$ paragraph, that the activity is promising), and without precising the quantity of secnidazole and of antibiotic required for the treatment.

When associated to secnidazole in the therapeutic indication and conditions of administration planned (single intake), spiramycine will be used at a dose of about 3 000 000 IU.

However preferably, as a macrolide antibiotic, azithromycine will be associated to secnidazole, at a dose between 750 and 1500 mg, preferably 1000 mg.

If we compare with the figures indicated above for RODOGYL® spiramycine, the oral treatment proposed by the invention consists in the administration of a single intake (=only one day), preferably of:

1000 mg azithromycine (i.e. 1.34 times the molar mass of this macrolide antibiotic), and 2000 mg secnidazole As we can see, a quantity of secnidazole slightly equivalent to the quantity of metronidazole allow not only to reduce from 3 days to 1 day the treatment duration, but also to divide by 3 the quantity of antibiotic administered.

According to the invention, the treatment can be over within one day (instead of 3-4 days) during which the patient will receive orally the pre-cited dose of secnidazole and either a single dose of 1000 mg azithromycine, either, preferably, two doses of about 500 mg azithromycine.

Secnidazole and the single dose (or first dose) of azithromycine will be administered simultaneously or at very close time intervals, and the possible second dose of azithromycine 12 hours after the first dose.

Preferably, secnidazole is in a powder form, and packed in sachet. Azithromycine can also be a powder packed in sachet, or a tablet.

In case of an administration of the antibiotic as a single daily dose, ideally the two active ingredients should be gathered in the same pharmaceutical oral form and, in that case, secnidazole powder and azithromycine powder will be mixed and packed in the same sachet, and the treatment will consist in the ingestion of the content of this only sachet.

For carrying out the invention, a kit can be proposed, containing in a packaging:

a pharmaceutical form adapted to oral administration and containing from 1500 mg to 2500 mg, preferably 2000 mg of secnidazole, and from 750 mg to 1500 mg, preferably 1000 mg of azithromycine, and a pharmaceutically acceptable excipient or diluent, or on one hand, a pharmaceutical form adapted to oral administration and containing from 1500 mg to 2500 mg, preferably 2000 mg of secnidazole, and a pharmaceutically acceptable excipient or diluent and, on the other hand, either one unit of a pharmaceutical form adapted to oral administration and containing 1000 mg azithromycine and a pharmaceutically acceptable excipient or diluent, or two units of a pharmaceutical form adapted to oral administration and each containing 500 mg azithromycine and a pharmaceutically acceptable excipient or diluent.

It is obvious that a treatment in one single day is more likely to be properly followed, and so to be active, rather than the present treatment on 3-4 days.

Moreover, a shortened treatment, using antibiotics of the macrolide type, leads to less resistant mutant germs. Finally, one might think that a shorter treatment leads to fewer side effects.

The invention extends to a pharmaceutical form adapted to oral administration, as a single dose, and containing from 1500 mg to 2500 mg secnidazole and a pharmaceutically acceptable excipient or diluent.

Preferably, this pharmaceutical form contains 2000 mg secnidazole.

Besides, the pharmaceutical form can contain about 1000 mg azithromycine.

The association according the invention has been tested in the following conditions:

The third molars may cause, during their eruption, local inflammatory manifestations called pericoronaritis. In acute forms, regional and general signs can be associated (fever, adenopathy, trismus), as well as possible complications of the cellulitis type by diffusion of the infection in the anatomic spaces around. Antibiotherapy is then justified, associated or not with a surgical procedure and, as stated above, the spiramycine-metronidazole association (RODOGYL® spiramycine or its alternative double dosed BIRODOGYL® (double of the RODOGYL) is mainly used till now for this purpose.

DB, dentist, facing patients with very rapid healing imperatives, prescribed upon the applicant suggestion and under confidentiality, 2 g secnidazole and 1 g azithromycine in one day, instead of BIRODOGYL® (double of the RODOGYL). The $3^{rd}$ day after treatment, he found that the oedema, festering and pain had disappeared, whereas, based on the secnidazole and azithromycine half-lives, of about 25 hours and about 20 hours respectively, the antibiotic treatment efficacy did not exceed 25 hours, instead of 96 hours required in the case of BIRODOGYL® (double of the RODOGYL).

He repeated the process with about ten other patients and found the same results.

This effect is unexpected because it is not directly linked to the half-lives of the drugs in the association.

It is clear that the invention is not limited to the use of spiramycine and azithromycine as antibiotic, as secnidazole can be associated to any convenient antibiotic, active against germs responsible for stomatologic infections.

The invention claimed is:

1. A method for treatment of a dental infection, the method comprising administering orally to a subject in need of treatment of a dental infection a composition comprising secnidazole and azithromycin.

2. The method according to claim 1, wherein the composition comprises from 1500 to 2500 mg of the secnidazole and a pharmaceutically acceptable excipient or diluent.

3. The method according to claim 2, wherein the composition comprises 750 mg to 1500 mg of azithromycin.

4. The method according to claim 2, wherein the composition comprises 500 mg of azithromycin.

* * * * *